United States Patent
Egami et al.

(10) Patent No.: US 8,305,087 B2
(45) Date of Patent: Nov. 6, 2012

(54) PARTICULATE MATTER DETECTION DEVICE

(75) Inventors: Takashi Egami, Tokoname (JP);
Takeshi Sakuma, Nagoya (JP);
Masahiro Tokuda, Nagoya (JP); Atsuo Kondo, Okazaki (JP)

(73) Assignee: NGK Insulators, Ltd., Nagoya (JP)

( * ) Notice: Subject to any disclaimer, the term of this patent is extended or adjusted under 35 U.S.C. 154(b) by 321 days.

(21) Appl. No.: 12/701,774

(22) Filed: Feb. 8, 2010

(65) Prior Publication Data

US 2010/0229629 A1    Sep. 16, 2010

(30) Foreign Application Priority Data

Mar. 12, 2009    (JP) ................. 2009-058856

(51) Int. Cl.
*G01N 27/62* (2006.01)
*G01N 27/00* (2006.01)
*G01F 13/00* (2006.01)

(52) U.S. Cl. ............ 324/464; 324/71.4; 73/861.41
(58) Field of Classification Search .......... 324/464, 324/459, 460, 71.4, 71.3, 71.1, 76.11; 73/28.02, 73/28.01, 861.41, 861; 250/397
See application file for complete search history.

(56) References Cited

U.S. PATENT DOCUMENTS

| | | | |
|---|---|---|---|
| 4,387,369 A * | 6/1983 | Klein et al. | 340/627 |
| 6,828,794 B2 * | 12/2004 | Reavell et al. | 324/464 |
| 7,145,320 B2 * | 12/2006 | Yoshida et al. | 324/71.4 |
| 2010/0000863 A1 * | 1/2010 | Kondo et al. | 204/406 |

FOREIGN PATENT DOCUMENTS

JP    60-123761 A1    7/1985

OTHER PUBLICATIONS

U.S. Appl. No. 12/715,598, filed Mar. 2, 2010, Tokuda, et al.
U.S. Appl. No. 12/715,617, filed Mar. 2, 2010, Tokuda, et al.
U.S. Appl. No. 12/715,644, filed Mar. 2, 2010, Tokuda, et al.
U.S. Appl. No. 12/715,661, filed Mar. 2, 2010, Tokuda, et al.

* cited by examiner

*Primary Examiner* — Hoai-An D Nguyen
(74) *Attorney, Agent, or Firm* — Burr & Brown

(57) ABSTRACT

A particulate matter detection device including a first electrode having one surface covered with a dielectric material; a second electrode which is disposed on the side of the one surface of the first electrode via a space where a gas including particulate matter flows and which performs one or both of the formation of a discharge and an electric field by a voltage applied between the first electrode and the second electrode; a pair of measurement electrodes disposed on the surface of the dielectric material so as to face each other; and a protective film disposed on the surfaces of the pair of measurement electrodes and having a volume resistivity of 10 Ωcm to $10^{12}$ Ωcm, where the variate of the electric properties between the pair of measurement electrodes is measured, and the amount of the collected particulate matter can be obtained.

14 Claims, 1 Drawing Sheet

PARTICULATE MATTER DETECTION DEVICE

BACKGROUND OF THE INVENTION

1. Field of the Invention

The present invention relates to a device which detects a particulate matter included in an exhaust gas from a diesel engine or the like.

2. Description of the Related Art

An exhaust gas from a diesel engine or the like includes a particulate matter ((PM) detected as three components of an organic solvent soluble component, soot and sulfate), and this particulate matter has been a cause for air pollution. In particular, when a defect occurs in a particulate matter generation source such as the diesel engine, the particulate matter in the exhaust gas discharged to atmospheric air increases, and noticeably adversely affects the environment. To prevent this problem, it is essential to detect the particulate matter in the exhaust gas and to recognize the defect in the diesel engine or the like.

Moreover, in recent years, to prevent the pollution and improve the environment, a diesel particulate filter (DPF) has been incorporated in an exhaust system or the like and used for the treatment of the exhaust gas. This DPF is usually made of a ceramic material, has a high reliability and hence can be used for a long period of time. However, it cannot be considered that there is not any possibility of the occurrence of a defect such as cracking due to heat deterioration or the like. If there is such a possibility, the particulate matter leaks though its amount is small. To prevent this problem, it is important to detect the particulate matter in the exhaust gas treated by the DPF and to immediately detect the occurrence of the defect.

It is to be noted that examples of a prior document include Patent Document 1. In Patent Document 1, a particulate matter detection device is disclosed in which the particulate matter is charged by corona discharge to measure the ion current thereof, thereby measuring the amount of the particulate matter.

[Patent Document 1] JP-A-60-123761

However, in the method described in Patent Document 1, the ion current for charging the particulate matter is weak, whereby a large-scale detection circuit for detecting the weak ion current is required, and the device becomes expensive. Additionally, when the flow rate of the exhaust gas is large, the particulate matter cannot effectively be charged, and a measured value is smaller than the amount of the particulate matter actually contained in the exhaust gas, whereby there is room for the improvement of precision. There has also been a problem that electrodes and the like are corroded by acid or alkali in the exhaust gas.

The present invention has been developed in view of such a situation, and an object thereof is to provide a particulate matter detection device which can easily and inexpensively detect the particulate matter, which has a high measurement precision and which is excellent in corrosion resistance of measurement electrodes.

SUMMARY OF THE INVENTION

To achieve the above object, according to the present invention, there is provided a particulate matter detection device as follows.

According to a first aspect of the present invention, a particulate matter detection device is provided, the device comprising: a first electrode having a plate-like shape and having one surface covered with a dielectric material; a second electrode which is disposed on the side of the one surface of the first electrode via a space where a gas including a particulate matter flows and which performs one or both of discharge and the formation of an electric field by a voltage applied between the first electrode and the second electrode; a pair of measurement electrodes disposed on the surface of the dielectric material so as to face each other; and a protective film disposed on the surfaces of the pair of measurement electrodes and having a volume resistivity of 10 $\Omega$cm to $10^{12}$ $\Omega$cm, wherein the variate of electric properties between the pair of measurement electrodes is measured to obtain the amount of the collected particulate matter.

According to a second aspect of the present invention, the particulate matter detection device according to the first aspect is provided, wherein the protective film is what is doped with a metal.

According to a third aspect of the present invention, the particulate matter detection device according to the first aspect is provided, wherein the protective film is formed of two layers of an insulating protective film disposed on the surfaces of the measurement electrodes and a low resistance film disposed on the surface of the insulating protective film and having a volume resistivity of $10^{-5}$ $\Omega$cm to 10 $\Omega$cm.

According to a fourth aspect of the present invention, the particulate matter detection device according to the first aspect is provided, wherein the protective film is an insulating protective film disposed on the surfaces of the measurement electrodes and including a plurality of fine metal pieces scattered on the surface thereof.

According to a fifth aspect of the present invention, the particulate matter detection device according to the first aspect is provided, wherein the protective film is an oxide film formed on the surfaces of the measurement electrodes.

According to a sixth aspect of the present invention, the particulate matter detection device according to any one of the first through fifth aspects is provided, wherein the electric properties are one or more electric properties selected from the electric property group consisting of a resistance, an inductance, a capacitance and an impedance.

According to a seventh aspect of the:present invention, the particulate matter detection device according to any one of the first through sixth aspects is provided, wherein the pair of measurement electrodes have a linear shape, and are disposed on the surface of the dielectric material so that the measurement electrodes face each other longly along a direction vertical to a direction in which the gas including the particulate matter flows.

According to an eighth aspect of the present invention, the particulate matter detection device according to the seventh aspect is provided, wherein each of the pair of measurement electrodes having the linear shape is branched into a plurality of portions, and has a plurality of facing portions.

Accordingto a ninth aspect of the present invention, the particulate matter detection device according to the eighth aspect is provided, wherein the pair of measurement electrodes having the plurality of facing portions are disposed over the whole surface of the dielectric material.

The particulate matter detection device of the present invention is a device disposed in a through channel through which the gas (the exhaust gas) including the particulate matter passes, to detect the particulate matter included in the gas. In the particulate matter detection device according to the present invention, the voltage is applied between the first electrode and the second electrode, thereby causing the second electrode to perform discharge, and consequently the particulate matter included in the gas flowing through the space between the first electrode and the second electrode is charged, or the beforehand charged particulate matter is collected on the surface of the protective film which covers the first electrode or the surfaces of both the protective film and the inter-electrode dielectric material provided with the first electrode. In this case, the particulate matter is deposited on the surface of the protective film which covers the first electrode or the surfaces of both the protective film and the inter-electrode dielectric material provided with the first electrode, and the electric properties between the pair of measurement electrodes disposed on the surface of the inter-electrode dielectric material vary while having a constant relation between the electric properties and the amount of the deposited particulate matter. To solve the problem, in the particulate matter detection device according to the present invention, the variate of the electric properties is acquired to obtain the amount of the particulate matter collected on the surface of the protective film or the surfaces of both the protective film and the inter-electrode dielectric material. Quantification can be performed, and hence needless to say, it is possible to judge whether or not the particulate matter in the gas flowing through the space is present (the amount is zero (0)). Therefore, the particulate matter detection device according to the present invention is referred to as the detection device. In the particulate matter detection device according to the present invention, the amount of the particulate matter included in the gas flowing through the space can be obtained by correction on the basis of the amount of the particulate matter, and the concentration of the particulate matter in the gas can be calculated from the relation between the amount and the flow rate of the gas flowing through the space. Furthermore, in the particulate matter detection device of the present invention, since the protective film having the volume resistivity of 10 $\Omega$cm to $10^{12}$ $\Omega$cm is disposed on the surfaces of the pair of measurement electrodes, it is possible to prevent the measurement electrodes from being corroded by an acid or alkali component in the exhaust gas. In addition, since the volume resistivity of the protective film is from 10 $\Omega$cm to $10^{12}$ $\Omega$cm, there is an advantage that the low-resistance particulate matter deposited on the protective film can electrically be recognized.

To detect, for example, the variate of the impedance as the electric property, the variate of a current of a 10 nanoampere (nA) level may be measured though the level varies in accordance with the size of a measurement frequency or a measurement voltage. Therefore, the particulate matter detection device of the present invention does not become expensive, but the detection of the particulate matter or the measurement of the amount thereof and the further measurement of the concentration thereof can easily be performed, and a measurement error is small. In addition, the detection of the particulate matter and the measurement of the amount and concentration thereof makes it possible to immediately detect the defect of a diesel engine or the like or the occurrence of the defect of a DPF, whereby the particulate matter detection device according to the present invention contributes to the decrease of the amount of the discharged particulate matter and the prevention of air pollution.

In the particulate matter detection device according to the present invention, since the measurement electrodes for measuring the electric properties are present on the surface of the same dielectric material, the degree of the setting freedom of a distance between the measurement electrodes is high, a high sensitivity can easily be obtained, and an arbitrary sensitivity can be obtained in accordance with an application.

DESCRIPTION OF THE PREFERRED EMBODIMENT

Figure 1:
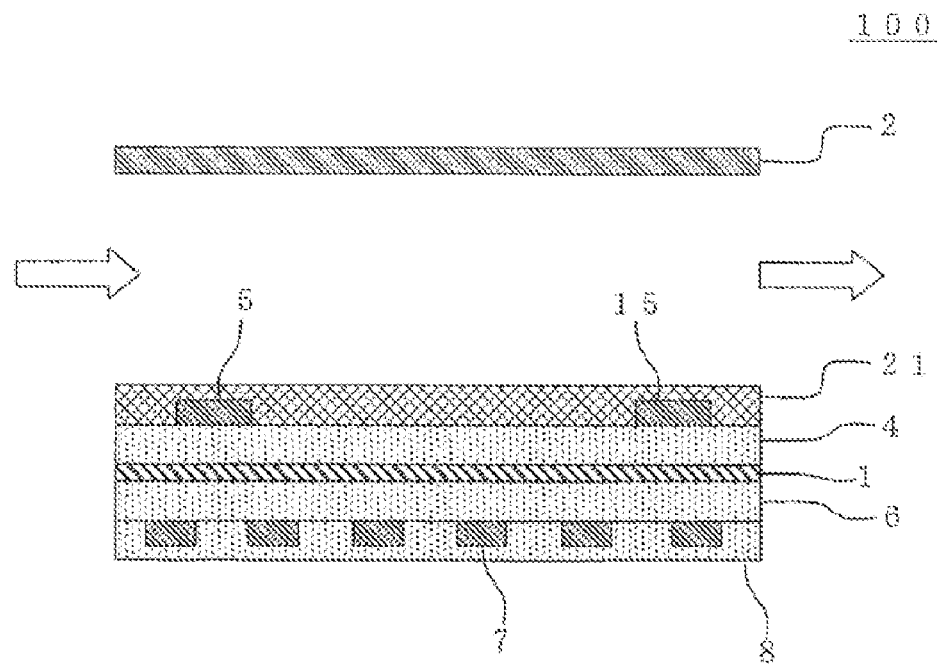
FIG. 1A is a schematic diagram showing the cross section of one embodiment of a particulate matter detection device of the present invention which is parallel to a gas flowing direction and which crosses a first electrode at right angles.
FIG. 1B is a plan view schematically showing the embodiment of the particulate matter detection device of the present invention.
Figure 1:
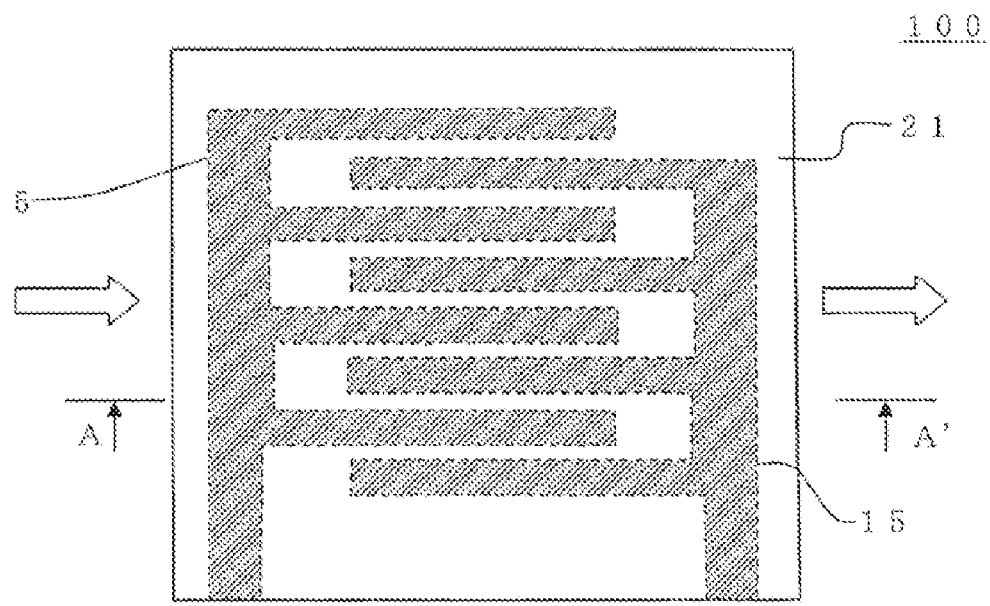

Hereinafter, an embodiment of the present invention will be described appropriately with reference to the drawings, but the present invention is not limited to the embodiment when interpreted. Various alterations, modifications, improvements or replacements may be added based on the knowledge of a person with ordinary skill without departing from the scope of the present invention. For example, the drawings show a preferable embodiment according to the present invention, but the present invention is not restricted by a configuration or information shown in the drawings. To carry out or verify the present invention, means similar or equivalent to that described in the present specification can be applied, and preferable means is described as follows.

[Particulate Matter Detection Device]

First, the constitution, function, operation and the like of a particulate matter detection device according to the present invention will mainly be described.

FIG. 1A is a schematic diagram showing the cross section of one embodiment of the particulate matter detection device of the present invention which is parallel to a gas flowing direction and which crosses a first electrode at right angles. FIG. 1B is a plan view schematically showing the embodiment of the particulate matter detection device of the present invention. It is to be noted that in FIG. 1B, a second electrode 2 is omitted. Moreover, FIG. 1A is a sectional view of the particulate matter detection device cut along the line A-A' of FIG. 1B.

As shown in FIGS. 1A and 1B, the particulate matter detection device of the present embodiment includes a first electrode 1 having a plate-like shape and having one surface covered with a dielectric material (an inter-electrode dielectric material) 4; the second electrode 2 which is disposed on the side of the one surface of the first electrode 1 via a space where a gas including a particulate matter flows and which performs one or both of discharge and the formation of an electric field by a voltage applied between the first electrode 1 and the second electrode; a pair of measurement electrodes 5, 15 disposed on the surface of the dielectric material (the inter-electrode dielectric material) 4 so as to face each other; and a protective film 21 disposed on the surfaces of the pair of measurement electrodes 5, 15 and having a volume resistivity of 10 $\Omega$cm to $10^{12}$ $\Omega$cm. Moreover, the variate of electric properties between the pair of measurement electrodes 5 and 15 is measured, whereby the amount of the collected particulate matter can be obtained. Here, "the collected particulate matter" is the particulate matter collected on the surface of the protective film 21 or both the surfaces of the protective film 21 and the dielectric material (the inter-electrode dielectric material) 4. That is, when the whole surfaces of the measurement electrodes 5, 15 and inter-electrode dielectric material 4 are covered with the protective film 21 as in the particulate matter detection device of the present embodiment, the particulate matter is the particulate matter collected on the surface of the protective film 21. When at least a part of the surface of the inter-electrode dielectric material 4 is not covered with the protective film 21 but is exposed to the space, the particulate matter is the particulate matter collected on the surfaces of both the protective film 21 and the inter-electrode dielectric material 4. It is to be noted that it is preferable from the viewpoint of durability that the whole surfaces of the measurement electrodes 5, 15 and inter-electrode dielectric material 4 are covered with the protective film 21. In a particulate matter detection device 100 of the present embodiment, since the protective film having a volume resistivity of 10 Ωcm to $10^{12}$ Ωcm is disposed on the surfaces of the pair of measurement electrodes, the measurement electrodes can be prevented from being corroded by an acid or alkali component in the exhaust gas.

In the particulate matter detection device 100 of the present embodiment, the volume resistivity of the protective film 21 provided on the surfaces of the pair of measurement electrodes 5, 15 is from 10 Ωcm to $10^{12}$ Ωcm, preferably from $10^8$ Ωcm to $10^{12}$ Ωcm, further preferably from $10^{10}$ Ωcm to $10^{12}$ Ωcm. Since the volume resistivity of the protective film 21 is in such a range, there is an advantage that the low-resistance particulate matter deposited on the protective film can electrically precisely be recognized. If the volume resistivity of the protective film 21 is smaller than 10 Ωcm, the low-resistance particulate matter deposited on the protective film cannot electrically precisely be recognized sometimes. If the volume resistivity of the protective film 21 is larger than $10^{12}$ Ωcm, the protective film having a stable volume resistivity cannot be manufactured, and a measurement precision increases owing to the fluctuation of the volume resistivity sometimes.

The thickness of the protective film 21 on the surfaces of the measurement electrodes 5, 15 is preferably from 10 to 500 μm, further preferably from 10 to 100 μm. Since the thickness of the protective film 21 on the surfaces of the measurement electrodes 5, 15 is in such a range, the measurement electrodes 5, 15 can be protected while keeping a high sensitivity. If the thickness of the protective film 21 on the surfaces of the measurement electrodes 5, 15 is smaller than 10 μm, the strength of the protective film 21 lowers sometimes. If the thickness is larger than 500 μm, the sensitivity lowers sometimes. Moreover, when the protective film 21 is also provided on the surface of the inter-electrode dielectric material 4, the thickness of the protective film 21 on the surface of the inter-electrode dielectric material 4 is preferably from 10 to 500 μm, further preferably from 10 to 100 μm. Since the thickness of the protective film 21 on the surface of the inter-electrode dielectric material 4 is in such a range, it is possible to obtain the particulate matter detection device 100 having the high sensitivity while keeping the strength of the protective film 21. If the thickness of the protective film 21 on the surface of the inter-electrode dielectric material 4 is smaller than 10 μm, the strength of the protective film 21 lowers sometimes. If the thickness is larger than 500 μm, the sensitivity lowers sometimes. As the material of the protective film 21, a metal oxide such as silica ($SiO_2$), alumina ($Al_2O_3$), zirconia ($ZrO_2$) or titania ($TiO_2$) is preferable.

The protective film 21 is preferably what is doped with a metal. Here, "doped with the metal" is a state in which a metal element having a high conductivity is substantially evenly disposed in the protective film for a purpose of controlling a volume resistance or a state in which the concentration of the metal element tilts in the thickness direction of the protective film from the surface thereof (the surface has a high concentration). When the protective film 21 is what is doped with the metal, the volume resistivity can easily be controlled. As the metal contained in the protective film 21, aluminum, silicon, titanium, gold, nickel, platinum or the like is preferable. The amount of the metal contained in the protective film 21 is preferably from 0.01 to 10 mol %, further preferably from 0.1 to 5 mol %. If the amount is smaller than 0.01 mol %, the volume resistivity increases sometimes. If the amount is larger than 10 mol %, the volume resistivity decreases owing to the uneven distribution of the doping metal sometimes.

The protective film 21 is preferably formed of two layers of an insulating protective film disposed on the surfaces of the measurement electrodes 5, 15 and a low resistance film disposed on the surface of the insulating protective film and having a volume resistivity of $10^{-5}$ Ωcm to 10 Ωcm. In this way, the protective film 21 is formed of the two layers of the insulating protective film and the low resistance film, whereby there is an advantage that even when the concentration of the particulate matter (deposited on the electrode protective film) is small, the measurement can be performed with a satisfactory sensitivity. As the material of the insulating protective film, a metal oxide such as silica ($SiO_2$), alumina ($Al_2O_3$), zirconia ($ZrO_2$) or titania ($TiO_2$) is preferable. The thickness of the insulating protective film is preferably from 10 to 500 μm, further preferably from 10 to 100 μm. If the thickness is smaller than 10 μm, the measurement electrodes under the low resistance film and the insulating protective film might short-circuit. If the thickness is larger than 500 μm, the sensitivity lowers sometimes. As the material of the low resistance film exposed to the surface, titanium, nickel, aluminum, silicon or diamond-like carbon (DLC) is preferable. Moreover, the low resistance film may be an ITO film (a transparent conductive film (a film made of a mixture of indium oxide and tin oxide)). The thickness of the low resistance film is preferably from 0.005 to 0.1 μm, further preferably from 0.005 to 0.05 μm. If the thickness is smaller than 0.005 μm, the strength lowers or the low resistance film becomes a discontinuous film, whereby an effect of improving the sensitivity cannot be obtained sometimes. If the thickness is larger than 0.1 μm, the sensitivity lowers sometimes.

The protective film 21 is preferably an insulating protective film disposed on the surfaces of the measurement electrodes 5, 15 and including a plurality of fine metal pieces scattered on the surface thereof. In this way, the protective film 21 has a structure where the plurality of fine metal pieces are scattered on the surface of the insulating protective film, which produces an advantage that even when the concentration of the particulate matter (deposited on the electrode protective film) is small, the measurement can be performed with a satisfactory sensitivity owing to a bridge effect by the scattered metal pieces. The plurality of fine metal pieces are disposed in the surface of the insulating protective film so as to be exposed on the surface thereof. As the material of the metal pieces, a metal such as titanium, nickel, aluminum, silicon, chromium, gold, platinum, silver, tungsten, tungsten plated with nickel or molybdenum plated with nickel is preferable. The size of each fine metal piece is preferably from 10 to 4000 $μm^2$, further preferably from 100 to 500 $μm^2$. If the size is smaller than 10 $μm^2$, the bridge effect by the scattered metal pieces is not exerted, and the measurement cannot be performed with the satisfactory sensitivity sometimes. If the size is larger than 4000 $μm^2$, the measurement can be performed with the satisfactory sensitivity owing to the bridge effect by the scattered metal pieces, but the dynamic range of the measurement of the amount of the deposited particulate matter cannot be obtained sometimes. The total area where the metal pieces are provided is preferably from 1 to 80% (in terms of area), further preferably from 30 to 60% of the whole surface of the protective film 21. The thickness of each of the metal pieces is preferably from 1 to 100 μm, further preferably from 5 to 50 μm. As the material of the insulating protective film, a metal oxide such as silica ($SiO_2$), alumina ($Al_2O_3$), zirconia ($ZrO_2$) or titania ($TiO_2$) is preferable. The thickness of the insulating protective film is preferably from 10 to 500 µm, further preferably from 10 to 100 µm. If the thickness is smaller than 10 µm, the strength lowers sometimes. If the thickness is larger than 500 µm, the sensitivity lowers sometimes.

The protective film 21 is preferably an oxide film formed on the surfaces of the measurement electrodes 5, 15.

When the protective film 21 is the oxide film, the durability of the electrodes advantageously improves. As the oxide film, a film formed by oxidizing the measurement electrodes 5, 15 is preferable. The thickness of the oxide film is preferably from 0.1 to 5 µm, further preferably 0.1 to 1 µm. If the thickness is smaller than 0.1 µm, the strength lowers sometimes. If the thickness is larger than 5 µm, the sensitivity lowers sometimes.

As shown in FIGS. 1A and 1B, the particulate matter detection device 100 of the present embodiment preferably further includes an electrode outside dielectric material 6 which covers the lower surface (the other surface) of the first electrode 1 in FIG. 1A, a heater 7 provided on the surface (the lower surface in FIG. 1) of the electrode outside dielectric material 6, and a sheet-like heat insulating material 8 which covers, protects and insulates the heater 7 from ambient air for keeping the heat. Moreover, the device preferably includes a collection power source which applies a voltage between the first electrode 1 and the second electrode 2, a heater power source which supplies a power to the heater 7, a property measurement unit (means) connected to the pair of measurement electrodes to measure the electric properties between the pair of measurement electrodes, a particulate matter amount calculation unit (means) which calculates the amount of the particulate matter, a particulate matter concentration calculation unit (means) which calculates the concentration of the particulate matter, a flow rate meter which measures the flow rate of a gas such as the exhaust gas flowing through the space between the first electrode 1 and the second electrode 2, and a control unit which controls the above units. The control unit is constituted of, for example, a sequencer having an electric signal input/output function and the like. The control unit has a function of inputting the electric signal of the flow rate measured by the flow rate meter in addition to the particulate matter concentration calculation unit, and performs the control of the whole device including the control of the heater power source or the collection power source, the switching of a measurement mode and the like.

In the particulate matter detection device 100 of the present embodiment, the exhaust gas including the particulate matter flows through a space between the inter-electrode dielectric material 4 which covers the plate-like first electrode 1 and the plate-like second electrode 2 from the left to the right as shown by arrows in FIG. 1A. The flow rate of this exhaust gas is measured by the flow rate meter. In this state, when, for example, a direct-current high voltage is applied to the second electrode 2 by the collection power source, discharge occurs, the exhaust gas (molecules) around the second electrode 2 is separated into plus and minus ions, and the minus ion moves toward the first electrode 1 to which a plus direct-current high voltage has been applied. At this time, the particulate matter included in the exhaust gas collides with and is charged with the minus ion. Moreover, the charged particulate matter is collected and deposited by an electrostatic force on the surface of the protective film 21 which covers the plus first electrode 1, or the surfaces of the protective film 21 and the inter-electrode dielectric material 4. In this case, the electric properties between the pair of measurement electrodes 5, 15 vary in accordance with the degree of the deposition of the particulate matter, and hence when the variate of the electric properties is known, the amount of the collected particulate matter (PM) is obtained. Moreover, the PM concentration of the exhaust gas is obtained from the amount of the deposited PM.

The electric properties measured by the measurement electrodes 5, 15 are one or more electric properties selected from the electric property group consisting of a resistance, an inductance, a capacitance and an impedance. For example, when the impedance is obtained as the electric property between the measurement electrodes 5, 15, the resistance, the capacitance and the inductance can be measured by use of an alternate-current power source, respectively. Furthermore, by use of a constant current source, the variate of the voltage between the measurement electrodes 5, 15 may be measured, thereby measuring the variate of the impedance. By use of a constant voltage source, the variate of the current flowing between the measurement electrodes 5, 15 or the variate of a charge accumulated between the measurement electrodes 5, 15 may be measured, thereby measuring the variate of the impedance between the measurement electrodes 5, 15. The property measurement unit can have an appropriate constitution in accordance with such a method for obtaining the electric properties and the variate thereof. The property measurement unit may be constituted of, for example, an alternate-current power source which applies a voltage between the measurement electrodes 5, 15, and a measuring instrument. Examples of a preferable measuring instrument include an LCR meter.

A distance between the protective film 21 and the second electrode 2 for forming the space through which the exhaust gas flows is preferably from 0.5 to 50 mm, more preferably from 0.6 to 40 mm. Such a distance makes it possible to more efficiently perform the discharge, thereby collecting the particulate matter. If the distance between the protective film 21 and the second electrode 2 is smaller than 0.5 mm, a collection ratio lowers, thereby lowering a measurement precision sometimes. If the distance is larger than 50 mm, a higher voltage is required, and hence energy is wasted sometimes.

In the particulate matter detection device 100 of the present embodiment, the first electrode 1 performs the discharge as a counter electrode of the second electrode 2, and performs a function of a member which sucks and collects the charged particulate matter. The plate-like first electrode 1 in the particulate matter detection device 100 preferably has a substantially rectangular shape, but may have a polygonal shape such as a pentangular shape, a round shape, an elliptic shape, a track-like shape, a shape provided with concaves/convexes on an outer periphery thereof, a shape provided with one slit or a plurality of slits or the like. The plate-like second electrode 2 preferably has a substantially rectangular shape in the same manner as in the first electrode 1, but may have a polygonal shape such as a pentangular shape, a round shape, an elliptic shape, a track-like shape, a shape provided with concaves/convexes on an outer periphery thereof, a shape provided with one slit or a plurality of slits or the like in the same manner as in the first electrode 1.

Here, the collection power source supplies a stable direct-current or alternate-current voltage so as to cause the discharge between the first electrode 1 and the second electrode 2. As the collection power source, for example, a power source using a power source circuit by a flyback system or the like can be employed. By this power source, energy from an input-side power source can be stored in a transformer, and the stored energy can be released to an output side, thereby supplying a direct-current high voltage. In the power source circuit of the flyback system, the storage and discharge of the energy in and from the transformer are controlled by a transistor or the like, and an output-side current is rectified by a diode.

In the particulate matter detection device 100 of the present embodiment, the measurement electrodes 5, 15 are provided so as to face each other, and measure the variate of the electric properties between the measurement electrodes 5, 15. A distance between the measurement electrodes 5 and 15 is set to such a range that the variate of the electric properties between the measurement electrodes 5, 15 caused by collecting the particulate matter by the first electrode 1 can clearly be measured. The distance is, for example, from about 0.2 to 10 mm.

The pair of measurement electrodes 5, 15 preferably have a linear shape, and each of the pair of measurement electrodes is branched into a plurality of portions, has a plurality of facing portions, and is provided on the surface of the dielectric material. That is, the pair of measurement electrodes 5, 15 are disposed so that each of the measurement electrodes 5, 15 is branched into a plurality of comb teeth-like portions and so that the plurality of portions corresponding to comb teeth of the measurement electrodes 5, 15 are alternately arranged. That is, the measurement electrodes 5, 15 are provided on the surface of the inter-electrode dielectric material 4 so that the tooth of the comb teeth-like measurement electrode 15 is sandwiched between the teeth of the comb teeth-like measurement electrode 5 and so that the plurality of comb teeth of the measurement electrodes 5, 15 engage with each other. In the particulate matter detection device of the present embodiment, the comb teeth-like measurement electrodes 5, 15 are thus provided so that the comb teeth engage with each other, which can improve the measurement sensitivity of the electric properties. Moreover, the particulate matter deposited on the inter-electrode dielectric material is not missed but can be detected, and the device is excellent in the precision of the measurement of the amount and concentration of the particulate matter. Furthermore, the pair of measurement electrodes 5, 15 may have a linear shape, may be disposed on the surface of the dielectric material so that the measurement electrodes face each other longly along a direction vertical to a direction in which the gas including the particulate matter flows. Moreover, a plurality of branched and facing portions of the measurement electrodes 5 and 15 are provided over the whole surface of the inter-electrode dielectric material 4. In the particulate matter detection device according to the present invention, from the viewpoint of the improvement of the measurement sensitivity and measurement precision of the electric properties, it is not preferable that the distance between the pair of facing measurement electrodes is long. On the other hand, the pair of facing measurement electrodes are preferably provided at positions corresponding to the whole space through which the exhaust gas flows. The thickness of each of the measurement electrodes 5, 15 is preferably from 10 to 500 µm, further preferably from 10 to 100 µm. If the thickness is smaller than 10 µm, close contact properties lower sometimes. If the thickness is larger than 500 µm, micro cracks occur in the electrodes and a base interface owing to the stress of the film, or warpage occurs in an element itself owing to the stress of the film sometimes.

When the measurement electrodes 5, 15 have the comb teeth-like shape as described above, the width of each of the plurality of branched portions corresponding to the comb teeth is preferably from 10 to 500 µm, further preferably from 50 to 200 µm. If the thickness is smaller than 10 µm, disconnection occurs sometimes. If the thickness is larger than 200 µm, an element area (a measurement electrode area) for obtaining a satisfactory element sensitivity becomes excessively large sometimes. Moreover, the length of each of the portions corresponding to the comb teeth is preferably from 2 to 50 mm, further preferably from 5 to 10 mm. If the length is smaller than 2 mm, the sensitivity lowers sometimes. If the length is larger than 50 mm, the particulate matter detection device becomes excessively large sometimes.

In the particulate matter detection device 100 of the present embodiment, the shape and size of the heater 7 may be determined so that all of the collected particulate matter on the surface of the inter-electrode dielectric material 4 can be burnt.

The heater 7 is used in not only a case where the particulate matter is oxidized and removed but also a case where the influence of water of dew condensation or the like is prevented from being exerted during the measurement of the variate of the electric properties between the measurement electrodes 5, 15. For example, during the detection of the impedance variate or the discharge, the measurement electrodes 5, 15 are appropriately heated, whereby the adhesion of the water onto the measurement electrodes 5, 15 can be prevented. At this time, a preferable heating temperature is from 200 to 300° C.

As the power source for the heater, from the viewpoint of enabling efficient temperature control, a power source of a step-down chopper type is preferable. An especially preferable power source is a step-down chopper type switching power source using a self arc suppressing type semiconductor switch. In this case, a preferable switching frequency is an audio frequency or more, that is, 20 kHz or more. Fuel consumption is directly influenced, and hence the current and power of the power source for the heater are preferably further decreased. Moreover, the preferable power source for the heater has a function of calculating the temperature of the heater 7 from the voltage and the current to control the temperature.

In the particulate matter detection device 100 of the present embodiment, the heat insulating material 8 suppresses the radiation of heat generated by the heater 7, which makes it possible to efficiently use the heat of the heater 7 for burning the particulate matter. The preferable thickness of the heat insulating material 8 is such a thickness that the heat radiation can be suppressed, and is, for example, from about 100 to 1000 µm.

[Material of Particulate Matter Detection Device]

Next, the material of each constituent element of the particulate matter detection device according to the present invention will be described with respect to the particulate matter detection device 100 as an example.

Examples of the preferable material of the first electrode 1, the second electrode 2, the measurement electrodes 5, 15 and a wiring line used for connecting them include a material containing at least one selected from the group consisting of gold, silver, copper, platinum, palladium, nickel, titanium, manganese, molybdenum and tungsten. The content ratio of each component is preferably 20 vol % or more, more preferably 60 vol % or more. Moreover, as the material of the first electrode 1, the second electrode 2, the measurement electrodes 5, 15 and the wiring line used for connecting them, stainless steel may be employed.

Examples of the preferable material of the inter-electrode dielectric material 4, the electrode outside dielectric material 6 and the heat insulating material 8 include a ceramic material including at least one selected from the group consisting of alumina, magnesium oxide, silicon oxide, silicon nitride, aluminum nitride, zirconia, cordierite, mullite, spinel, aluminum-titanium-based oxide, magnesium-calcium-titanium-based oxide, barium-titanium-zinc-based oxide and barium-titanium-based oxide. A ceramic-glass composite material which is obtained by mixing the above ceramic material with a glass component and which can be fired at a low temperature may be used. The inter-electrode dielectric material 4 and electrode outside dielectric material 6 made of such a ceramic material do not easily break down even if a temperature fluctuation occurs, and are excellent in resistance to thermal shock. Examples of the heat insulating material 8 include a ceramic material including at least one selected from the group consisting of alumina, magnesium oxide, silicon oxide, silicon nitride, aluminum nitride, zirconia, cordierite, mullite, spinnel, aluminum-titanium-based oxide, magnesium-calcium-titanium-based oxide, barium-titanium-zinc-based oxide and barium-titanium-based oxide. A ceramic-glass composite material which is obtained by mixing the above ceramic material with a glass component and which can be fired at a low temperature may be used. Moreover, the material may be porous or fibrous.

Examples of the preferable material of the heater 7 include platinum, copper, nickel, titanium, manganese, tungsten, molybdenum and tungsten carbide. In particular, platinum exhibits a high precision in a relation between a resistance value and a temperature, and hence the use of this material as the material of the heater 7 enables precise temperature control.

[Manufacturing Method of Particulate Matter Detection Device]

Next, a manufacturing method of the particulate matter detection device according to the present invention will be described with respect to the preparation of the particulate matter detection device 100 as an example.

First, the preferable ceramic material of the inter-electrode dielectric material 4, the electrode outside dielectric material 6 and the heat insulating material 8 is mixed with a binder, a plasticizer, a dispersant, water and a solvent such as an organic solvent if necessary, thereby preparing a slurry-like forming material. During the mixing, an alumina pot and an alumina ball, or a mono ball (a ball mill) may be used. The materials of the inter-electrode dielectric material 4, the electrode outside dielectric material 6 and the heat insulating material 8 may have the same composition or different compositions. A foaming agent is preferably added to the forming material of the heat insulating material 8.

As to the binder, as an aqueous binder, methylcellulose, polyvinyl alcohol, polyethylene oxide or the like can preferably be used, and as a non-aqueous binder, polyvinyl butyral, acrylic resin, polyethylene, polypropylene or the like can preferably be used. Examples of the acrylic resin include (meth)acrylic resin, a (meth)acrylic ester copolymer and an acrylic ester-methacrylic ester copolymer. From the viewpoint of the suppression of the occurrence of cracking during the subsequent green sheet forming, drying and firing, the amount of the binder to be added is preferably from 3 to 20 parts by mass, especially preferably from 6 to 17 parts by mass with respect to 100 parts by mass of the ceramic material.

Examples of the preferable plasticizer include glycerin, polyethylene glycol, dibutyl phthalate, di-2-ethylhexyl phthalate and di-isononyl phthalate. The amount of the plasticizer to be added is preferably 30 to 70 parts by mass, especially preferably from 45 to 55 parts by mass with respect to 100 parts by mass of binder. If the amount is larger than 70 parts by mass, a green sheet becomes excessively soft, and is easily deformed in a process of processing the sheet. If the amount is smaller than 30 parts by mass, the green sheet becomes excessively hard. If the sheet is simply bent, the sheet is cracked. In this way, handling properties deteriorate sometimes.

Examples of the preferable dispersant include aqueous dispersants such as an anionic surfactant, wax emulsion and pyridine, and non-aqueous dispersants such as a fatty acid, ester phosphate and a synthetic surfactant. The amount of the dispersant to be added is preferably from 0.5 to 3 parts by mass, especially preferably from 1 to 2 parts by mass with respect to 100 parts by mass of ceramic material. If the amount is smaller than 0.5 part by mass, the dispersion properties of the ceramic material lower sometimes, and cracking or the like occurs in the green sheet sometimes. If the amount is larger than 3 parts by mass, the dispersion properties of the ceramic material do not vary but impurities during firing increase.

Examples of the preferable organic solvent (the solvent) include xylene and butanol. The organic solvent may be used alone or as a mixture of a plurality of solvents. The amount of the solvent to be added is preferably from 50 to 200 parts by mass, especially preferably from 75 to 150 parts by mass with respect to 100 parts by mass of ceramic material.

Then, a slurry-like forming material is stirred under a reduced pressure, defoamed, and prepared so as to have a predetermined viscosity. From the viewpoint that the material is easily formed into a sheet-like material, the viscosity as a value measured by a B-type viscosity meter is preferably from 2.0 to 6.0 Pa·s, more preferably from 3.0 to 5.0 Pa·s, especially preferably from 3.5 to 4.5 Pa·s.

Next, the obtained forming material is formed into the sheet-like material to form the green sheet for forming the inter-electrode dielectric material 4, the electrode outside dielectric material 6 and the heat insulating material 8 later. A preferable forming method is a doctor blade method, a press forming method, a rolling method, a calendar roll method or the like. The thickness of the green sheet is preferably from 50 to 800 μm.

Then, the surface of the obtained green sheet is provided with a conductive paste for forming the first electrode 1, the pair of measurement electrodes 5, 15, the heater 7 and a necessary wiring line later. Moreover, the green sheets are laminated to obtain a green laminate. The conductive paste can be obtained by adding the binder and a solvent such as terpineol to powder made of the preferable material for forming the first electrode 1, the pair of measurement electrodes 5, 15, the heater 7 and the necessary wiring line and sufficiently kneading the powder by use of a tri-roll mill or the like. Conductive paste providing means is preferably a screen printing method. The conductive paste is provided specifically by printing the conductive paste for forming the first electrode 1 and the necessary wiring line on one surface of the green sheet for forming the electrode outside dielectric material 6, laminating the further green sheet for forming the inter-electrode dielectric material 4, and printing the measurement electrodes 5, 15 and the necessary wiring line in a desired pattern on the surface of the green sheet for forming the inter-electrode dielectric material 4. On the other hand, the conductive paste for forming the heater 7 and the necessary wiring line is printed on the other surface of the green sheet for forming the electrode outside dielectric material 6, and the further green sheet for forming the heat insulating material 8 is laminated (see FIG. 1). The green sheets are preferably laminated while being pressurized.

Next, the obtained green laminate is dried at 60 to 150° C. If the organic binder is contained, the laminate is degreased at 400 to 800° C., and then fired at 1200 to 1600° C. In this way, the fired laminate is obtained which includes the first electrode 1, the inter-electrode dielectric material 4, the measurement electrodes 5, 15, the electrode outside dielectric material 6, the heater 7 and the heat insulating material 8 to constitute the particulate matter detection device 100.

The protective film 21 is preferably formed by screen-printing the protective film on the surface of the portion of the green laminate on which the measurement electrodes 5, 15 have been printed, and drying, degreasing and then firing the green laminate. Moreover, after forming the fired laminate, the protective film may be formed by chemical vapor deposition (CVD) (a chemical gas-phase reaction film forming method). Moreover, in a case where the protective film made of the two layers of the insulating protective film and the low resistance film is formed, the protective film is preferably formed by a method of forming the insulating protective film by the screen printing on the surface of the portion of the green laminate on which the measurement electrodes 5, 15 have been printed, drying, degreasing and firing the green laminate, and then forming the low resistance film on the surface of the insulating protective film by the CVD. Furthermore, to form the protective film 21 made of the insulating protective film including a plurality of fine metal pieces scattered on the surface thereof, the protective film is preferably formed by a method of screen-printing the insulating protective film on the surface of the portion of the green laminate on which the measurement electrodes 5, 15 have been printed, forming the plurality of fine metal pieces on the surface of the insulating protective film by the screen printing, and drying, degreasing and then firing the green laminate.

As the second electrode 2, a commercially available thin plate made of the above preferable material is purchased, used and integrated with the fired laminate via a support member. As the second electrode, the laminate of the ceramic material and the conductive paste may be used. As this support member, the sintered member made of the above preferable material of the inter-electrode dielectric material 4, the electrode outside dielectric material 6 and the heat insulating material 8 may be used.

Moreover, a laminate structure may be formed by integrating the fired laminate and the support member of the second electrode 2 so as to form a cavity (the space) through which the exhaust gas including the particulate matter flows. In this case, before obtaining the fired laminate, on the side of the inter-electrode dielectric material 4 (the measurement electrodes 5, 15) of the green laminate, the green sheet for forming the cavity and the green sheet for forming the top plate may further be laminated, and the conductive paste for forming the second electrode 2 and the necessary wiring line later may be provided on the inner surface (the surface facing the cavity) of the green sheet for forming the top plate to obtain the whole green laminate, followed by drying, necessary degreasing and firing.

As the collection power source, the property measurement unit and the power source for the heater, commercially available units which meet the above preferable specifications are purchased. As the flow rate meter, a commercially available meter may be employed. The collection power source is connected to the first electrode 1 and the second electrode 2, the property measurement unit is connected to the measurement electrodes 5, 15, and the power source for the heater is connected to the heater 7. The particulate matter amount calculation unit and the particulate matter concentration calculation unit may be constituted of software in a computer such as a sequencer. The control unit may be constituted of software and a control circuit (hardware) in a computer such as a sequencer so as to realize the operation of the particulate matter detection device 100 described above or later. As described above, the particulate matter detection device 100 can be prepared.

[Method of Using Particulate Matter Detection Device]

Next, a method of using the particulate matter detection device according to the present invention will be described with respect to a case where the particulate matter detection device 100 is used as an example.

(Collection Process) First, a sensor portion of the particulate matter detection device 100 is disposed in, for example, an exhaust system (an exhaust gas pipe) of a diesel engine, and is brought into a usable state by performing power supply, control line connection and the like. Then, for example, a direct-current high voltage is applied between the second electrode 2 and the first electrode 1 by the collection power source, and the particulate matter is charged and deposited on the surface of the protective film 21.

A time for applying the high voltage is preferably from 0.5 to 120 seconds, more preferably from 2 to 10 seconds. If the time is shorter than 0.5 second, the amount of the collected particulate matter decreases, and hence the measurement precision of the amount of the particulate matter lowers sometimes. If the time is longer than 120 seconds, the amount of the collected particulate matter increases, and hence the amount of the particulate matter cannot easily correctly be grasped from the detected variate of the impedance.

The preferable voltage to be supplied to the first electrode 1 and the second electrode 2 varies with the distance between the electrodes, but the voltage to be applied is raised to strength the electric field, thereby improving a collection force. On the other hand, insulation, an insulating distance and the like raise problems, and the device enlarges. Therefore, for practical purpose, the voltage is preferably 10 kV or less.

A current flowing between the first electrode 1 and the second electrode 2 owing to the discharge is preferably 1 mA or less, further preferably from 1 to 100 $\mu$A. If the current is smaller than 1 $\mu$A, a collection ratio decreases sometimes.

A used power directly influences the fuel consumption, and hence is preferably small. Moreover, in view of the decrease of generated electromagnetic noise or the size of a circuit for causing the discharge, the used power is preferably 10 W or less, more preferably 1 W or less.

(Measurement Process) After the completion of the deposition of the particulate matter, the application of the high voltage between the second electrode 2 and the first electrode 1 is stopped, and the property measurement unit is operated to measure the variate of the impedance between the measurement electrodes 5, 15 preferably for about 1 to 60 seconds. By this variate of the impedance, the amount and concentration of the particulate matter are obtained. It is to be noted that as described above, the variate of the impedance between the measurement electrodes 5, 15 can be measured while depositing the particulate matter (applying the high voltage) on the surface of the protective film 21. However, this is regarded as another measurement mode.

When the property measurement unit is constituted of the alternate-current power source for applying the voltage between the measurement electrodes 5, 15 and the measuring instrument, the value of the voltage to be applied from the alternate-current power source is preferably from 1 to 60 V, more preferably from 2 to 30 V. If the value is smaller than 1 V, a detection signal becomes small, and is easily influenced by the noise. If the value is larger than 60 V, a general-purpose IC cannot be used sometimes. A measurement frequency is preferably 300 kHz or less.

(Removal Process) After the completion of the measurement of the variate of the impedance between the measurement electrodes 5, 15, the heater 7 is operated by the power source for the heater to oxidize and remove the particulate matter deposited on the surface of the protective film 21.

When the power source for the heater is the step-down chopper type switching power source, a current to be supplied to the heater 7 is preferably from about 0.8 to 4 A, and the used power is preferably 48 W or less.

A time for oxidizing and removing the particulate matter by the heater 7 is preferably from 1 to 600 seconds, especially preferably from 3 to 120 seconds. If the time is shorter than one second, the oxidation removal of the particulate matter becomes insufficient sometimes. If the time is longer than 600 seconds, energy is wasted sometimes.

A temperature during the oxidizing and removing of the particulate matter collected on the surface of the protective film 21 by the heater 7 is preferably from 500 to 900° C., especially preferably from 550 to 700° C. If the temperature is lower than 500° C., the particulate matter is not easily oxidized and removed sometimes. If the temperature is higher than 900° C., the life of the element shortens sometimes.

As described above, the collection process, the measurement process and the removal process are repeated, whereby the detection of the particulate matter can stably be continued for a long period of time. It is to be noted that in a case where the exhaust gas from the diesel engine is a particulate matter detection target, the discharge is preferably performed when conditions such as the revolution number and torque of the diesel engine and the flow rate and temperature of the exhaust gas become specific conditions. These conditions can be judged by the control unit (the sequencer or the like) by inputting the information of the diesel engine as a signal into the control unit, and providing a temperature meter in the exhaust gas pipe to input the information of the meter as a signal into the control unit.

EXAMPLES

Hereinafter, the present invention will further specifically be described with respect to examples, but the present invention is not limited to these examples.

Example 1

(Preparation of Forming Material)

Alumina was used as a ceramic material, polyvinyl butyral was used as a binder, di-2-ethylhexyl phthalate was used as a plasticizer, sorbitan trioleate was used as a dispersant, and an organic solvent (xylene:butanol=6:4 (mass ratio)) was used as a dispersion medium. These materials were placed and mixed in an alumina pot, to prepare a slurry-like forming material for preparing a green sheet. As to the used amounts of the materials, with respect to 100 parts by mass of alumina, 7 parts by mass of binder, 3.5 parts by mass of plasticizer, 1.5 parts by mass of dispersant and 100 parts by mass of organic solvent were used.

Next, the obtained slurry-like forming material for preparing the green sheet was stirred under a reduced pressure, defoamed and prepared so as to have a viscosity of 4 Pa·s. The viscosity of the slurry was measured by a B-type viscosity meter.

(Formation Processing)

Next, the slurry-like forming material obtained by the above method was processed and formed into a sheet-like material by use of a doctor blade method. At this time, a cutting portion forming green sheet was also prepared so as to form a through hole (a space formed between a first electrode and a second electrode) when green sheets were laminated. The thickness of the green sheet was 250 μm.

On the surface of the obtained green sheet, as shown in FIGS. 1A and 1B, electrodes, a heater and a wiring line were formed. A conductive paste for forming the electrodes, the heater and the wiring line to be provided was prepared by adding, to platinum powder, 2-ethyl hexanol as a solvent, polyvinyl butyral as a binder, di-2-ethylhexyl phthalate as a plasticizer, sorbitan trioleate as a dispersant, alumina as the co-base of the green sheet and glass frit as a sintering auxiliary agent, and sufficiently kneading the materials by use of a stone mill and a tri-roll mill (at a mass ratio of platinum:alumina:glass frit:2-ethyl hexanol:polyvinyl butyral:di-2-ethylhexyl phthalate:sorbitan trioleate=80:15:5:50:7:3.5:1). Moreover, a conductive paste for forming the heater was prepared by adding, to platinum powder, 2-ethyl hexanol as a solvent, polyvinyl butyral as a binder, di-2-ethylhexyl phthalate as a plasticizer, sorbitan trioleate as a dispersant, alumina as the co-base of the green sheet and glass frit as a sintering auxiliary agent, and sufficiently kneading the materials by use of the stone mill and the tri-roll mill (at a mass ratio of platinum:alumina:glass frit:2-ethyl hexanol:polyvinyl butyral:di-2-ethylhexyl phthalate:sorbitan trioleate=80:15:5:50:7:3.5:1). The conductive pastes formed in this manner were printed on the surfaces of the green sheets by screen printing to prepare electrodes having a predetermined shape and the like.

To laminate the green sheets, the green sheets were pressurized and laminated by using a heatable uniaxial press, to obtain an unfired material (a green laminate) of a particulate matter detection device made of the laminate of the green sheets. It is to be noted that in FIG. 1A, the second electrode is exposed to the space, but in the present example, the second electrode was formed so as to be sandwiched between two green sheets, and the second electrode was embedded in a dielectric material.

Afterward, a portion for forming a protective film was formed on the surface the portions of the green laminate for forming measurement electrodes by screen printing. The screen printing was performed by using trade name TSU4060 manufactured by Seritech Co. The material of the protective film was silica. Moreover, the thickness of the protective film was measured by using a stylus step meter, and was 50 μm.

(Firing)

The obtained green laminate (the unfired material of the particulate matter detection device) was dried at 120° C. and fired at 1500° C. to prepare the particulate matter detection device. The obtained particulate matter detection device had a rectangular parallelepiped shape of 0.7 cm×0.2 cm×12 cm. The cross section of the through hole vertical to an exhaust gas circulating direction had a 10 cm×0.5 cm rectangular shape. Moreover, the volume resistivity of the protective film was $10^{11}$ Ωcm. The volume resistivity is measured by using MCP-T610 and MCP-HT450 manufactured by Mitsubishi Chemical Analytech. A film having a volume resistivity of $10^{-3}$ Ωcm or more and less than $10^6$ Ωcm is measured by the former device, and a film having a volume resistivity of $10^6$ to $10^{13}$ Ωcm is measured by the latter device. When the volume resistivity is unknown, both the devices are used. For the measurement of the volume resistivity, test pieces subjected to the same process are used. Each test piece has a structure including a green sheet as a base material, a round electrode made of the same material as that of the measurement electrode and a protective film disposed on the electrode. When the volume resistivity is less than $10^6$ Ωcm, a four-terminal four-probe device is brought into contact with the protective film to measure a resistance value, and the thickness of the protective film is measured from a sectional SEM photograph of the test piece to calculate the volume resistivity of the protective film. When the low resistance film is disposed on the protective film, the four-terminal four-probe device is brought into contact with the low resistance film on the protective film, and the thickness of the low resistance film is measured from a sectional SEM photograph of the test piece to calculate the volume resistivity of the low resistance film. When the volume resistivity of the protective film is $10^6$ Ωcm or more, a double measurement electrode and a guard electrode are formed on the protective film by Au sputtering to measure the volume resistivity of the protective film. The above measured volume resistivity of the protective film was a value measured by this method.

As a power source for discharge, a pulse power source and a DC power source were used. As a property measurement unit for measuring an impedance between the electrodes, an impedance analyzer manufactured by Agilent Technologies was used. The obtained particulate matter detection device was subjected to the measurement of the sensitivity (the sensitivity measurement) of the particulate matter detection device and the corrosion test of the measurement electrodes by the following methods. Results are shown in Table 1. It is to be noted that in Table 1, an initial capacitance and a capacitance after collection for one minute are shown, and a difference between the initial capacitance and the capacitance after the collection for one minute is a sensitivity.

(Sensitivity Measurement)

The obtained particulate matter detection device was disposed in an exhaust pipe of a diesel engine. As the diesel engine, a direct-jet diesel engine of 2000 cc displacement was used, and an exhaust gas was generated on conditions including a revolution number of 1500 rpm, a torque of 24 N·m, an exhaust gas recirculation (EGR) open degree of 50%, an exhaust gas temperature of 200° C. and suction air of 1.3 m³ (in terms of room temperature)/minute. The amount of a particulate matter in the exhaust gas by Smoke Meter (trade name: model 4158 manufactured by AVL Co.) was 2.0 mg/m³. The particulate matter was detected as follows. Before charging and collecting the particulate matter while generating the exhaust gas from the diesel engine, an initial capacitance (pF) between a pair of electrodes was measured six times for one minute. Afterward, the particulate matter was charged and collected for one minute. Afterward, the charging and collecting operation was stopped. Again, the capacitance (the capacitance between the pair of electrodes after the collection for one minute) (pF) was measured six times for one minute. As each of the initial capacitance and the capacitance after the collection for one minute, the average value of six measured values was obtained. Moreover, a difference between the initial capacitance and the capacitance after the collection for one minute is the index of the sensitivity of the particulate matter detection device. That is, the sensitivity is satisfactory as a value obtained by subtracting the initial capacitance from the capacitance after the collection for one minute is large. It is to be noted that in the present measurement, the burning of the particulate matter by the heater was not performed. When the particulate matter was charged and collected, the voltage to be applied by the high voltage power source was DC 2.0 kV, and during the measurement of the capacitance between the electrodes, a voltage to be applied from a measurement portion was AC 2 V, and a frequency thereof was 10 kHz.

(Corrosion Test)

The corrosion test of the measurement electrode (the element) was performed by the following method. First, the element heated to 350° C. was immersed into nitric acid of 0.013 mol/L for 60 minutes, the element heated to 350° C. was immersed into sulfuric acid of 0.0059 mol/L for 60 minutes, and the element heated to 350° C. was immersed into ammonia water of 0.0049 mol/L for 60 minutes, followed by washing with flowing water and drying, whereby the capacitance variate ratio of the measurement electrode was measured. As to the number of samples for the corrosion test, n=5 samples were used in each of examples and a comparative example. The capacitance variate ratio was obtained by dividing the difference between the capacitance of the measurement electrode before the corrosion test and the capacitance of the measurement electrode after the corrosion test by the capacitance of the measurement electrode before the corrosion test.

TABLE 1

|  | | Capacitance value (pF) | Corrosion test |
|---|---|---|---|
| Example 1 | Initial | 3 | Less than 1% |
|  | After collection for 1 min. | 4.3 |  |
| Example 2 | Initial | 3.2 | Less than 1% |
|  | After collection for 1 min. | 4.8 |  |
| Example 3 | Initial | 3.8 | Less than 1% |
|  | After collection for 1 min. | 6.5 |  |
| Example 4 | Initial | 3.9 | Less than 1% |
|  | After collection for 1 min. | 6.7 |  |
| Example 5 | Initial | 2.2 | Less than 1% |
|  | After collection for 1 min. | 3.3 |  |
| Comparative Example 1 | Initial | 2 | 12.3% ± 2.5% |
|  | After collection for 1 min. | 3 |  |

Example 2

A particulate matter detection device was prepared in the same manner as in Example 1 except that a protective film was what was doped with a metal. The protective film doped with the metal was prepared as follows. The preparation method of the protective film was similar to that of Example 1, but silica and titania were used as the materials of the protective film, and a blend ratio of titania ($TiO_2$) with respect to base silica ($SiO_2$) in terms of Ti atoms was 5 mol %. The volume resistivity of the protective film was $10^8$ Ωcm. In the same manner as in Example 1, sensitivity measurement and corrosion test were performed. Results are shown in Table 1.

Example 3

A particulate matter detection device was prepared in the same manner as in Example 1 except that a protective film was formed of two layers of an insulating protective film and a low resistance film. The protective film formed of the two layers of the insulating protective film and the low resistance film was prepared as follows. The insulating protective film was formed by screen printing on the surface of a portion of a green laminate on which measurement electrodes 5, 15 were printed, and the green laminate was dried and fired in the same manner as in Example 1, followed by forming the low resistance film on the surface of the insulating protective film by CVD. The screen printing was performed by using trade name TSU4060 manufactured by Seritech Co. Moreover, the CVD was performed by using trade name Super 7 manufactured by Universal Technics Co., Ltd. The material of the insulating protective film was silica, and the material of the low resistance film was diamond-like carbon (DLC). Furthermore, the thickness of the insulating protective film was 60 µm, and the thickness of the low resistance film was 0.2 µm. The volume resistivity of the protective film was 0.3 Ωcm. In the same manner as in Example 1, sensitivity measurement and corrosion test were performed. Results are shown in Table 1.

Example 4

A particulate matter detection device was prepared in the same manner as in Example 1 except that a protective film was formed of an insulating protective film having a plurality of fine metal pieces scattered on the surface thereof. The protective film including the insulating protective film having the plurality of fine metal pieces scattered on the surface thereof was prepared as follows. The insulating protective film was screen-printed on the surface of the portion of a green laminate on which measurement electrodes 5, 15 were printed. Afterward, the plurality of fine metal pieces were formed on the surface of the insulating protective film by screen printing, and then the green laminate was dried and fired in the same manner as in Example 1. The screen printing was performed by using trade name "TSU4060" manufactured by Seritech Co. The material of the insulating protective film was silica, the material of the metal pieces was tungsten, and nickel plating was performed after the drying and firing. The thickness of the insulating protective film was 45 µm, and the size of each metal piece was from about 100 to 200 µm$^2$. Moreover, an area where the metal pieces were provided was 10% of the area of the insulating protective film. The volume resistivity of the protective film was $10^{12}$ Ωcm. In the same manner as in Example 1, sensitivity measurement and corrosion test were performed. Results are shown in Table 1.

Example 5

A particulate matter detection device was prepared in the same manner as in Example 1 except that a protective film was an oxide film formed on the surfaces of measurement electrodes. A method of forming the oxide film on the surfaces of the measurement electrodes was as follows. An element was heated at 600° C. for three hours in an atmospheric furnace having a drying oxygen atmosphere, and subjected to an oxidation treatment. The thickness of the oxide film was 3 µm. The volume resistivity of the protective film was $10^9$ Ωcm. In the same manner as in Example 1, sensitivity measurement and corrosion test were performed. Results are shown in Table 1.

Comparative Example 1

A particulate matter detection device was prepared in the same manner as in Example 1 except that any protective film was not formed. In the same manner as in Example 1, sensitivity measurement and corrosion test were performed. Results are shown in Table 1.

It is seen from Table 1 that the particulate matter detection devices of Examples 1 to 5 keep a satisfactory sensitivity. Moreover, it is seen that they are excellent in corrosion resistance because the capacitance variate of the measurement electrodes after the corrosion test is 1% or less within a measurement error range. It is seen that the particulate matter detection device of Comparative Example 1 has a satisfactory sensitivity but has a poor corrosion resistance as compared with the particulate matter detection devices of Examples 1 to 5.

The particulate matter detection device of the present invention can preferably be utilized as means for detecting the particulate matter included in the exhaust gas or the like from the diesel engine, a flue or the like.

[Description of Reference Numerals]

1: first electrode, 2: second electrode, 4: inter-electrode dielectric material, 5, 15: measurement electrode, 6: electrode outside dielectric material, 7: heater, 8: heat insulating material, 21: protective film, and 100: particulate matter detection device.

What is claimed is:

1. A particulate matter detection device comprising:
   a first electrode having a plate-like shape and having one surface covered with a dielectric material;
   a second electrode which is disposed on the side of the one surface of the first electrode via a space where a gas including a particulate matter flows and which performs one or both of discharge and the formation of an electric field by a voltage applied between the first electrode and the second electrode;
   a pair of measurement electrodes disposed on the surface of the dielectric material so as to face each other; and
   a protective film disposed on the surfaces of the pair of measurement electrodes and having a volume resistivity of 10 Ωcm to $10^{12}$ Ωcm, wherein the protective film is formed of two layers of an insulating protective film disposed on the surfaces of the measurement electrodes and a low resistance film disposed on the surface of the insulating protective film and having; a volume resistivity of $10^{-5}$ Ωcm to 10 Ωcm,
   wherein the variate of electric properties between the pair of measurement electrodes is measured to obtain the amount of the collected particulate matter.

2. The particulate matter detection device according to claim 1, wherein the protective film is what is doped with a metal.

3. The particulate matter detection device according to claim 1, wherein the pair of measurement electrodes have a linear shape, and are disposed on the surface of the dielectric material so that the measurement electrodes face each other longly along a direction vertical to a direction in which the gas including the particulate matter flows.

4. The particulate matter detection device according to claim 1, wherein the protective film is an insulating protective film disposed on the surfaces of the measurement electrodes and including a plurality of fine metal pieces scattered on the surface thereof.

5. The particulate matter detection device according to claim 1, wherein the protective film is an oxide film formed on the surfaces of the measurement electrodes.

6. The particulate matter detection device according to claim 1, wherein the electric properties are one or more electric properties selected from the electric property group consisting of a resistance, an inductance, a capacitance and an impedance.

7. The particulate matter detection device according to claim 2, wherein the electric properties are one or more electric properties selected from the electric property group consisting of a resistance, an inductance, a capacitance and an impedance.

8. The particulate matter detection device according to claim 3, wherein each of the pair of measurement electrodes having the linear shape is branched into a plurality of portions, and has a plurality of facing portions.

9. The particulate matter detection device according to claim 8, wherein the pair of measurement electrodes having the plurality of facing portions are disposed over the whole surface of the dielectric material.

10. The particulate matter detection device according to claim 2, wherein the pair of measurement electrodes have a linear shape, and are disposed on the surface of the dielectric material so that the measurement electrodes face each other longly along a direction vertical to a direction in which the gas including the particulate matter flows.

11. The particulate matter detection device according to claim 10, wherein each of the pair of measurement electrodes having the linear shape is branched into a plurality of portions, and has a plurality of facing portions.

12. The particulate matter detection device according to claim 4, wherein the electric properties are one or more electric properties selected from the electric property group consisting of a resistance, an inductance, a capacitance and an impedance.

13. The particulate matter detection device according to claim 5, wherein the electric properties are one or more electric properties selected from the electric property group consisting of a resistance, an inductance, a capacitance and an impedance.

14. The particulate matter detection device according to claim 11, wherein the pair of measurement electrodes having the plurality of facing portions are disposed over the whole surface of the dielectric material.

* * * * *